United States Patent [19]

Forsström

[11] 4,171,715
[45] Oct. 23, 1979

[54] TRANSPORTATION DEVICE FOR SUCCESSIVELY MOVING A NUMBER OF SAMPLE CONTAINERS PAST A TREATMENT POSITION

[75] Inventor: Bo G. Forsström, Järfälla, Sweden

[73] Assignee: LKB-Produkter AB, Bromma, Sweden

[21] Appl. No.: 828,990

[22] Filed: Aug. 30, 1977

[30] Foreign Application Priority Data

Sep. 7, 1976 [SE] Sweden ............................ 7609858

[51] Int. Cl.² ............................................. B65B 43/50
[52] U.S. Cl. ................................... 141/130; 198/341
[58] Field of Search ............ 23/253 R, 259; 198/341; 141/129, 130, 283, 284, 324

[56] References Cited

U.S. PATENT DOCUMENTS

| 3,038,340 | 6/1962 | Isreeli | 141/130 X |
| 3,945,412 | 3/1976 | Forsstrom | 198/341 X |

Primary Examiner—Richard E. Aegerter
Assistant Examiner—Frederick R. Schmidt
Attorney, Agent, or Firm—Fisher, Christen & Sabol

[57] ABSTRACT

A device for transporting containers arranged in a spiral path past a fixed treatment station includes a carriage to support the containers in their spiral path, with a driving mechanism which rotates the carriage about a vertical axis while simultaneously shifting the axis in a horizontal direction to bring the containers successively to a predetermined location. The driving mechanism also includes a sensing device which can control the starting and stopping of the carriage's movements.

4 Claims, 1 Drawing Figure

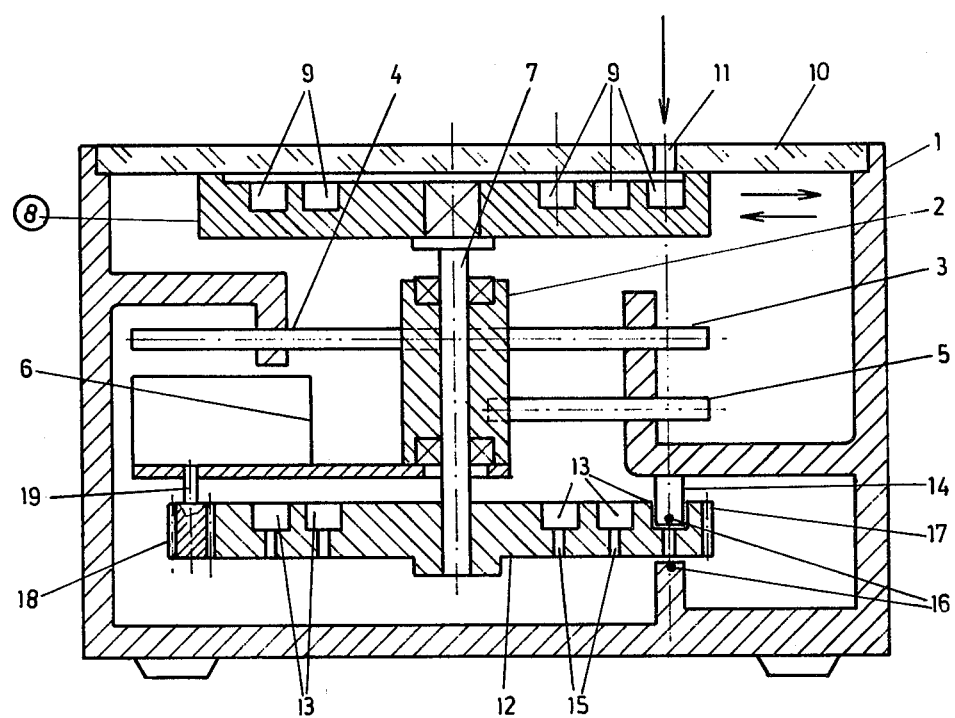

TRANSPORTATION DEVICE FOR SUCCESSIVELY MOVING A NUMBER OF SAMPLE CONTAINERS PAST A TREATMENT POSITION

The present invention refers to a transportation device for successively moving a number of sample containers past a treatment position, for instance for adding liquid to the containers or sucking liquid from the containers. In different types of laboratory work automatic transportation devices are used for passing samples past treatment- or measuring positions. One such transportation device are the so-called fraction collectors, i.e. devices where a number of test tubes successively are brought past an output mouthpiece from for instance a chromatography- or electrophoresis column so as to distribute substances separated in the column into different test tubes for further analysis. This type of sample transportation devices is usually also suited for use as so-called samplers, i.e. a device where liquid by means of a mouthpiece successively are sucked from a number of test tubes.

A great number of fraction collector designs are known, using different patterns of movement for the test tubes as well as for the mouthpieces. In one such design the test tubes are arranged in concentric rings in a turnable holder, whereby the mouthpiece is radially displaceable between the rings. An example of such a fraction collector is shown in the U.S. Pat. No. 2,894,542. The drawback of this type of fraction collectors is firstly that the driving means for moving the test tubes and the mouthpiece and the synchronization of these movements are rather complicated, and secondly that such fraction collectors usually require a constant turning angle of the test tube holder between the different positions which means that the distance between the test tubes increases with increasing radius of the rings. A design which however eliminates both these problems is shown in the U.S. Pat. No. 3,945,412, corresponding to Swedish Pat. No. 7402104-9 which describes a fraction collector where the test tubes are arranged in a spiral and where the radial movement of the mouthpiece is achieved by means of a groove running along the spiral, the groove being provided with means connected to the mouthpiece and where furthermore this groove is provided with marking indicating the positions of the vessels, said marking controlling the rotational movement so that the test tubes can be arranged close to one another with a decreasing angle of rotation as the periphery of the spiral is approached. In this fraction collector the mouthpiece will however be moving along a curved line across the test tube spiral which is a drawback for instance in cases where one wishes to protect the test tubes not subject to treatment from for instance pollution in the air. In these cases it is obviously desirable that the filling mouthpiece is stationary, so that the protection could be obtained by means of a cover arranged over the test tubes and being provided with a hole at the sample treatment position.

It is an object of the present invention to provide a sample transportation device suitable for use for instance as a fraction collector or a sampler, by which in addition to the advantages provided by the above cited Swedish patent one also has a stationary position of treatment which makes it possible for those sample vessels which are not in the treatment position to be protected from outside contamination. The characteristics of the invention will thereby appear from the claims attached to the specification.

The invention will now be described in detail reference being made to the enclosed drawing which shows a cross section through a device according to the invention.

In the drawing, reference 1 denotes a holder in which a carriage 2 is horizontally displaceable along three axes 3, 4 and 5 which are running in bores in the holder. To the carriage is also connected a driving means 6. In the carriage is furthermore a vertical axis 7 journalled, said axis carrying an upper plate 8 provided with a number of test tubes 9 arranged along a spiral. On the holder above the plate 8 is a sealing cover plate 10 arranged, said plate being provided with a hole 11 at the position of treatment. The journalled axis 7 is furthermore provided with a guiding plate 12 provided with an upper spiral groove 13 which is located exactly below the spiral line along which the test tubes 9 are arranged. In the groove 13 a guiding head 14 connected to the cover 1 is running. A plate 12 is furthermore along its periphery provided with gears 17 coupled to a gear wheel 18 which is connected to the motor axis 19 of the driving means 6. In the guiding groove 13 and furthermore holes 15 arranged, said holes being located exactly below the sample holders 9 and being detectable from a detecting device 16 for example a light admitting diode and a photo cell which are arranged on the guiding head 14 and the holder 1.

The above described device operates in the following manner. When the motor 6 makes the plate 12 rotate, this plate will in addition to its rotation also be displaced horizontally when the guiding head 14 follows the groove 13. Thereby is achieved that the different sample containers 9 successively will be located under the treatment position 11. By means of the holes 15 which are located exactly below the respective sample containers 9 and the hole detecting device 16 the rotation can thereby be controlled in such a way that a container 9 is located exactly below the hole 11. The output signal from the detecting device 16 is thus connected in such a way that its appearance stops the motor. The restart of the motor can then be made in a suitable way either for instance after a certain predetermined time or it can be controlled by some other parameter.

We claim:

1. Transportation device for successively moving a number of sample containers past a fixed sample treatment position for dispensing or removing liquid into or from said containers, characterized therein that it comprises a carriage mounted in a holder for horizontal displacement in a straight line, a horizontal plate provided with a series of sample containers arranged in a spiral line with respect to a central location, driving means for rotating said plate with respect to said carriage about a vertical shaft concentric with said central location, said driving means being mounted for displacement with said carriage, guiding means comprising two relatively movable interengaging elements, one of said elements being a guide plate connected to said carriage and said horizontal plate by said vertical shaft, said guide plate having a spiral line parallel with the spiral line defined by said sample containers, the other of said two elements being a guide head in engagement with said guide plate spiral line and being fixed with respect to the holder, means connecting said guide plate to said drive means to rotate said guide plate about said vertical shaft and thus rotate said horizontal plate displacing said horizontal plate during said rotation to place successive sample containers at said sample treatment position, said guide plate being also provided with positional markings corresponding to the positions of said containers along said horizontal plate spiral line for actuating a control means for the driving means.

2. Transportation device according to claim 1, characterized therein that on top of the sample containers is arranged a stationary sealing plate which seals the top openings of the sample containers and is provided with a hole at the sample treatment position.

3. Transportation device according to claim 1, characterized therein that the spiral line is constituted by a groove in which a stationary guiding head is running.

4. Transportation device according to claim 1, characterized therein that the positional markings are optically detectable.